(12) United States Patent
Cowley

(10) Patent No.: US 11,259,832 B2
(45) Date of Patent: Mar. 1, 2022

(54) ULTRASONIC HORN FOR AN ULTRASONIC SURGICAL INSTRUMENT, ULTRASONIC SURGICAL INSTRUMENT INCLUDING THE SAME, AND METHOD OF MANUFACTURING AN ULTRASONIC HORN

(71) Applicant: COVIDIEN LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 746 days.

(21) Appl. No.: 15/882,079

(22) Filed: Jan. 29, 2018

(65) Prior Publication Data

US 2019/0231384 A1 Aug. 1, 2019

(51) Int. Cl.
*A61B 17/32* (2006.01)
*A61B 17/22* (2006.01)
(Continued)

(52) U.S. Cl.
CPC .............. *A61B 17/320092* (2013.01); *A61B 17/22004* (2013.01); *A61B 17/320068* (2013.01); *A61B 2017/00402* (2013.01); *A61B 2017/00477* (2013.01); *A61B 2017/00526* (2013.01); *A61B 2017/00734* (2013.01); *A61B 2017/22015* (2013.01); *A61B 2017/320074* (2017.08); *B22F 3/225* (2013.01)

(58) Field of Classification Search
CPC ...... A61B 17/22004; A61B 17/320068; A61B 17/320092; A61B 2017/00402; A61B 2017/00477; A61B 2017/00526; A61B 2017/00734; A61B 2017/22015; A61B 2017/320074

See application file for complete search history.

(56) References Cited

U.S. PATENT DOCUMENTS 1,813,902 A 7/1931 Bovie
2,235,274 A 3/1941 Trehern
(Continued)

FOREIGN PATENT DOCUMENTS

EP 0705570 A1 4/1996
EP 908148 A1 4/1999
(Continued)

OTHER PUBLICATIONS

European Search Report dated Mar. 28, 2019, issued in EP Appln. No. 19153890.
(Continued)

*Primary Examiner* — Tigist S Demie
(74) *Attorney, Agent, or Firm* — Carter, DeLuca & Farrell LLP

(57) ABSTRACT

An ultrasonic horn for an ultrasonic transducer assembly of an ultrasonic surgical instrument includes a body and a nose. The body defines a tubular configuration having a hollow interior and a plurality of slots therethrough extending into the hollow interior. The nose extends distally from the body. The body defines a proximal connector configured to enable the body to be secured to a piezoelectric stack and the nose defines a distal connector configured to enable the nose to be engaged with a waveguide for transmission of ultrasonic energy produced by the piezoelectric stack to the waveguide.

8 Claims, 3 Drawing Sheets

(51) Int. Cl.
　　　A61B 17/00　　　(2006.01)
　　　B22F 3/22　　　(2006.01)

(56) References Cited

U.S. PATENT DOCUMENTS

| | | |
|---|---|---|
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,043,229 B2 | 10/2011 | Mulvihill et al. |
| 8,435,258 B2 | 5/2013 | Young et al. |
| 8,672,959 B2 | 3/2014 | Witt et al. |
| 2001/0048855 A1 | 12/2001 | Lin |
| 2002/0002379 A1 | 1/2002 | Bishop |
| 2002/0055754 A1 | 5/2002 | Ranucci et al. |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0041220 A1* | 2/2006 | Boukhny ............ A61F 9/00745 604/22 |

(56) References Cited

U.S. PATENT DOCUMENTS

| | | |
|---|---|---|
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0172076 A1* | 7/2008 | Chon ............... A61F 9/00745 606/169 |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2010/0324581 A1* | 12/2010 | Mackool ............ A61F 9/00745 606/169 |
| 2012/0078278 A1 | 3/2012 | Bales, Jr. et al. |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2016/0331397 A1* | 11/2016 | Parham ........... A61B 17/320068 |
| 2017/0143398 A1* | 5/2017 | Young ............... A61B 17/1659 |
| 2017/0296216 A1 | 10/2017 | Du et al. |
| 2018/0055529 A1* | 3/2018 | Messerly ............ B29C 65/4805 |

FOREIGN PATENT DOCUMENTS

| | | |
|---|---|---|
| EP | 1 594 209 A1 | 11/2005 |
| EP | 1707131 A1 | 10/2006 |
| EP | 1990032 A1 | 11/2008 |
| EP | 2 200 145 A1 | 6/2010 |
| EP | 2510891 A1 | 10/2012 |
| JP | 2000-506430 A | 5/2000 |
| JP | 2001-112768 A | 4/2001 |
| JP | 2001514541 A | 9/2001 |
| JP | 2002-518067 A | 6/2002 |
| JP | 2003-502102 A | 1/2003 |
| JP | 2003-285008 A | 10/2003 |
| JP | 2004-129871 A | 4/2004 |
| JP | 2005-278932 A | 10/2005 |
| JP | 2005-296411 A | 10/2005 |
| JP | 2009-538710 A | 11/2009 |
| WO | 2006/087885 A1 | 8/2006 |
| WO | 2006/119376 A2 | 11/2006 |
| WO | 2007/047380 A2 | 4/2007 |
| WO | 2007-080723 A1 | 7/2007 |
| WO | 2010049684 A1 | 5/2010 |
| WO | 2015041849 A2 | 3/2015 |

OTHER PUBLICATIONS

European Search Report dated Mar. 28, 2019, issued in EP Appln. No. 19155222.

Second Chinese Office Action issued in corresponding Chinese Application No. 201910088623.1 dated Dec. 9, 2021.

* cited by examiner ic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.
ULTRASONIC HORN FOR AN ULTRASONIC SURGICAL INSTRUMENT, ULTRASONIC SURGICAL INSTRUMENT INCLUDING THE SAME, AND METHOD OF MANUFACTURING AN ULTRASONIC HORN

BACKGROUND

Technical Field

The present disclosure relates to ultrasonic surgical instruments and, more particularly, to an ultrasonic horn for an ultrasonic surgical instrument, an ultrasonic surgical instrument including the same, and a method of manufacturing an ultrasonic horn.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an ultrasonic horn for an ultrasonic transducer assembly of an ultrasonic surgical instrument. The ultrasonic horn includes a body and a nose. The body defines a tubular configuration having a hollow interior and a plurality of slots extending into the hollow interior. The nose extends distally from the body. The body defines a proximal connector configured to enable the body to be secured to a piezoelectric stack and the nose defines a distal connector configured to enable the nose to be engaged with a waveguide for transmission of ultrasonic energy produced by the piezoelectric stack to the waveguide.

In an aspect of the present disclosure, the body and the nose are monolithically formed as a single component from a zirconium-based amorphous metal.

In another aspect of the present disclosure, the ultrasonic horn defines a total mass of less than about 80 g. The ultrasonic horn may define a thickness of each wall thereof of between about 0.6 mm and about 4 mm. Additionally or alternatively, the ultrasonic horn may define a total length of less than about 100 mm.

In another aspect of the present disclosure, the plurality of slots are elongated slots equally-spaced about the body between a proximal end portion of the body and a node point defined towards a distal end of the body.

In still another aspect of the present disclosure, the nose tapers in a proximal-to-distal direction.

In yet another aspect of the present disclosure, the nose is of solid construction except for the distal connector and defines a diameter between about 0.6 mm and about 4 mm.

An ultrasonic surgical instrument provided in accordance with aspects of the present disclosure includes a handle assembly including a housing and an ultrasonic transducer assembly supported by the housing. The ultrasonic transducer assembly including a piezoelectric stack and an ultrasonic horn secured to and extending distally from the piezoelectric stack. The ultrasonic horn includes a body defining a tubular configuration having a hollow interior and a plurality of slots extending into the hollow interior, and a nose extending distally from the body. The ultrasonic surgical instrument further includes an elongated assembly extending distally from the handle assembly and including a waveguide configured to engage the nose of the ultrasonic horn. The waveguide defines a blade at a distal end thereof. Ultrasonic energy produced by the piezoelectric stack is transmitted along the horn and the waveguide to the blade for treating tissue adjacent the blade.

In aspects, the ultrasonic horn may be configured similar to any of the aspects detailed above or otherwise herein.

A method of manufacturing a transducer assembly for an ultrasonic surgical instrument in accordance with aspects of the present disclosure includes forming, via metal injection molding, an ultrasonic horn including a body and a nose extending distally from the body. The body defines a tubular configuration having a hollow interior and a plurality of slots extending into the hollow interior. The method further includes securing a piezoelectric stack to a proximal end portion of the body of the ultrasonic horn.

In an aspect of the present disclosure, the ultrasonic horn is formed from a zirconium-based amorphous metal.

In another aspect of the present disclosure, the ultrasonic horn is formed to define a total mass of less than about 80 g and/or a thickness of each wall of the horn of between about 0.6 mm and about 4 mm.

In still another aspect of the present disclosure, securing the piezoelectric stack includes bolting the piezoelectric stack to the proximal end portion of the body of the ultrasonic horn.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

Figure 1:
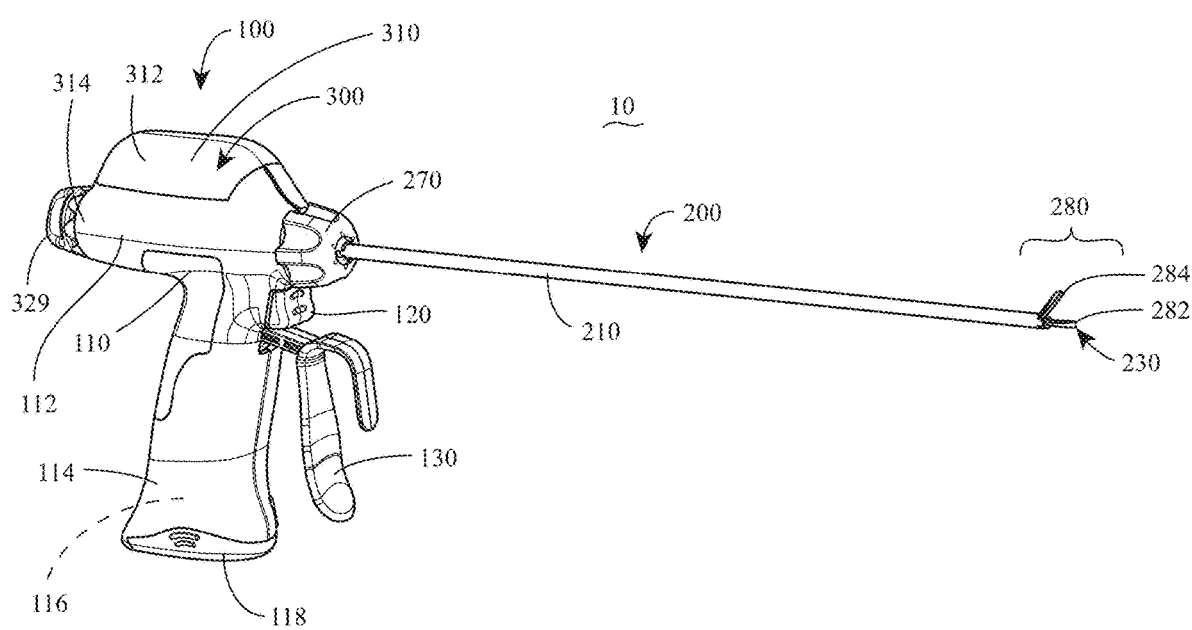
FIG. 1 is a side, perspective view of an ultrasonic surgical instrument provided in accordance with the present disclosure.
Figure 2:
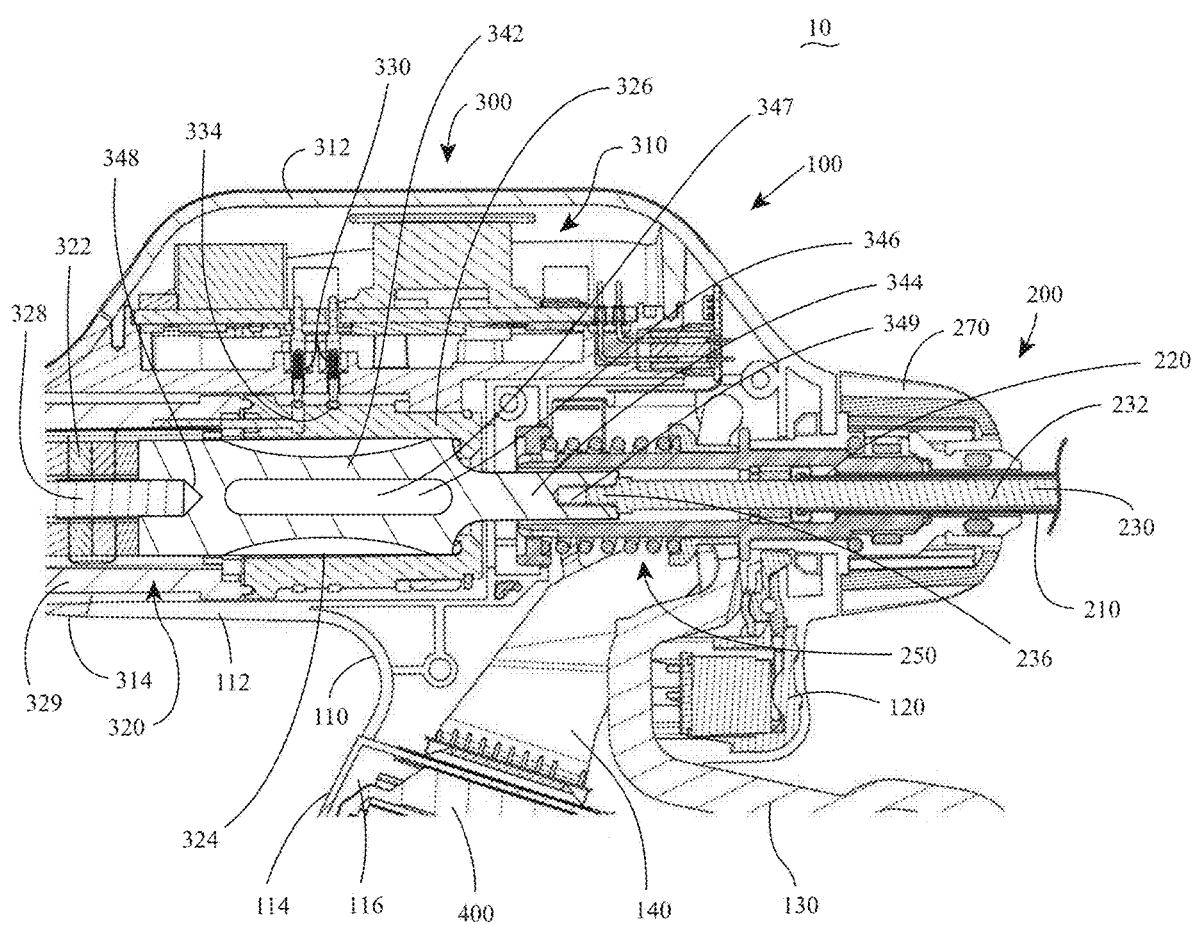
FIG. 2 is an enlarged, side, longitudinal, cross-sectional view of a proximal portion of the ultrasonic surgical instrument of FIG. 1 including an ultrasonic horn in accordance with the present disclosure coupling the transducer assembly with the waveguide.

Referring to FIGS. 1 and 2, ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator 310 and an ultrasonic transducer 320. TAG 300 may be permanently engaged with body portion 112 of housing 110 or removable therefrom. Generator 310 includes a housing 312 configured to house the internal electronics of generator 310, and a cradle 314 configured to rotatably support ultrasonic transducer 320. Alternatively, generator 310 may be remotely disposed and coupled to ultrasonic surgical instrument 10 by way of a surgical cable.

Ultrasonic transducer 320 includes a piezoelectric stack 322, a horn 324, a casing 326, and a bolt 328 securing piezoelectric stack 322 between horn 324 and a proximal nut (not shown). Horn 324 is described in greater detail below. Ultrasonic transducer 320 further includes a rotation knob 329 (FIG. 1). Casing 326 and rotation knob 329 are engaged with one another and cooperate to form an enclosure to encapsulate the proximal nut, piezoelectric stack 322, and a portion of horn 324, with the remainder of horn 324 extending distally from casing 326. Rotation knob 329 is accessible from the exterior of handle assembly 100 and is configured for manual rotation to rotate ultrasonic transducer 320 relative to generator 310 and housing 110.

A set of connectors 330 and corresponding rotational contacts 334 associated with generator 310 and ultrasonic transducer 320, respectively, enable drive signals to be communicated from generator 310 to piezoelectric stack 322 of ultrasonic transducer 320 to drive ultrasonic transducer 320 regardless of the rotational orientation of ultrasonic transducer 320. Horn 324, in turn, is configured to transmit the ultrasonic energy produced by piezoelectric stack 322 to waveguide 230 of elongated assembly 200 for transmission therealong to blade 282 of end effector 280 of elongated assembly 200, as detailed below.

Referring still to FIGS. 1 and 2, fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator 310 is remote from ultrasonic surgical instrument 10, battery assembly 400 and the configuration of fixed handle portion 114 for receiving battery assembly 400 need not be provided, as generator 310 may be powered by a standard wall outlet or other power source.

Elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230, as noted above, extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 349 of horn 324 such that ultrasonic motion produced by ultrasonic transducer 320 is transmitted along waveguide 230 to blade 282 for treating tissue clamping between blade 282 and jaw 284 or positioned adjacent to blade 282.

Figure 3:
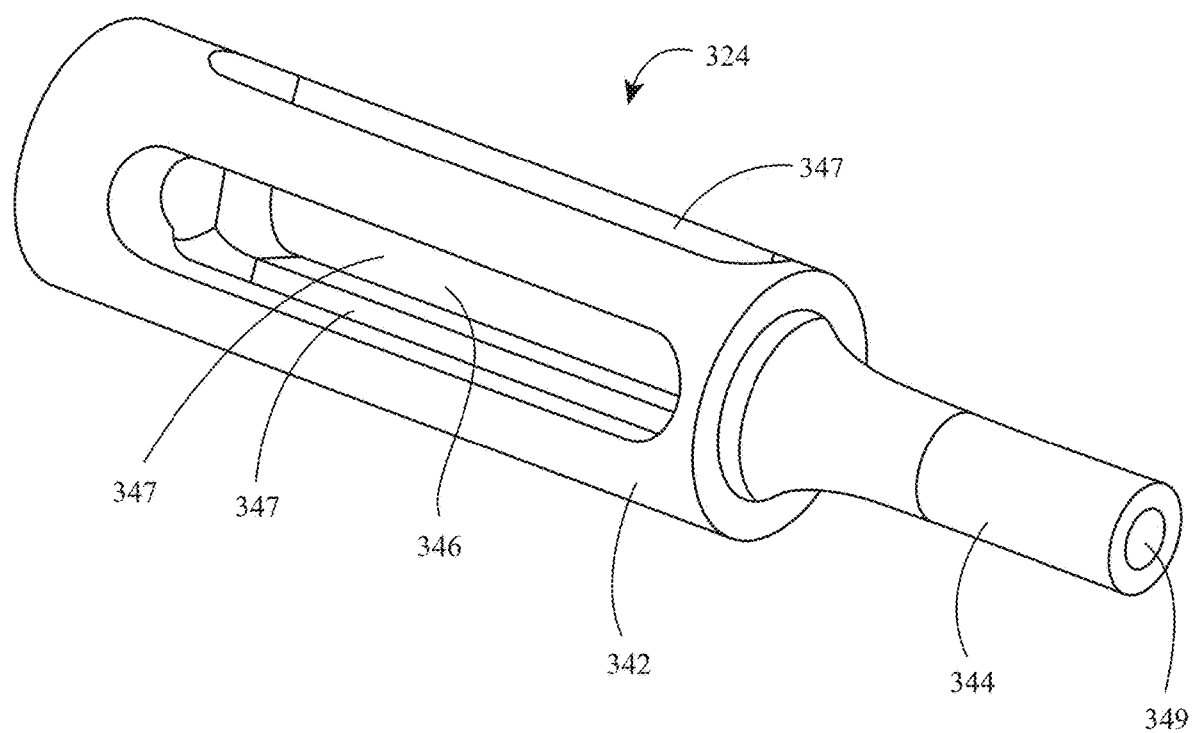
FIG. 3 is a side, perspective view of the ultrasonic horn of FIG. 2.

Turning now to FIGS. 2 and 3, ultrasonic horn 324 is configured in such a manner that ultrasonic horn 324 may be formed via metal injection molding (MIM) instead of the traditional method of machining which is expensive due to the tight tolerance requirements of ultrasonic horns. Ultrasonic horn 324, more specifically, may be formed via MIM using zirconium-based amorphous metals, although other suitable metals are also contemplated. In order to enable ultrasonic horn 324 to be formed via MIM, the volume and thickness of ultrasonic horn 324 must be below threshold levels to ensure the material can be injection molded and rapidly cooled within a mold. Specifically, it has been found that current manufacturing threshold levels for MIM of zirconium-based amorphous metals are: 80 g total mass, 0.6 mm to 4 mm wall thickness, and 100 mm total length. Thus, to ensure proper formation of ultrasonic horn 324 via MIM, ultrasonic horn 324 should define a total mass of less than about 80 g (wherein "about" accounts for manufacturing and material tolerances), a wall thickness of from about 0.6 mm to about 4 mm (wherein "about" accounts for manufacturing and material tolerances), and a total length of less than about 100 mm (wherein "about" accounts for manufacturing and material tolerances).

Ultrasonic horn 324 includes a body 342 and a nose 344 extending distally from body 342. Ultrasonic horn 324 defines a total length of less than about 100 mm. Body 342 defines a tubular configuration having a substantially uniform (within manufacturing and material tolerances) diameter along the entire length thereof. However, other configurations are also contemplated, e.g., cone-shaped. Body 342 defines a hollow interior 346 and a wall thickness of the tubular wall surrounding hollow interior 346 of from about 0.6 mm to about 4 mm. Body 342 further defines a plurality of slots 347 through the tubular wall thereof and extending into hollow interior 346. Body 342, more specifically, defines four equally-spaced elongated slots 347 having arched ends so as to define four equally-spaced, longitudinally-extending, and substantially parallel columns of body 342 that extend between the proximal end portion of body 342, which defines a proximal receiver 348 configured to receive bolt 328 to secure piezoelectric stack 322 between horn 324 and the proximal nut (see FIG. 2), and a node point defined along body 342 towards a distal end of body 342. However, other suitable number and/or configuration of slots 347 is also contemplated to define a corresponding configuration of body 342 extending between the proximal end portion thereof and the node point thereof towards the distal end of body 342. Slots 347, along with hollow interior 346, enable ultrasonic horn 324 to define a total mass of less than about 80 g and a wall thickness of from about 0.6 mm to about 4 mm.

Nose 344 of horn 324, as noted above, extends distally from body 342. Nose 344 tapers in proximal-to-distal direction along a portion of the length thereof and defines a threaded female receiver 349 configured to receive proximal threaded male connector 236 of waveguide 230 to permit releasable engagement of waveguide 230 with horn 324. Nose 344, having a reduced diameter as compared with body 342, may be of solid construction (except for threaded female receiver 349) in embodiments where the diameter of nose 344 does not exceed 4 mm. Alternatively, nose 344 may define a hollow or partially-hollow configuration such that a wall thickness of any portion thereof does not exceed 4 mm.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a handle assembly including a housing and an ultrasonic transducer assembly supported by the housing, the ultrasonic transducer assembly including a longitudinally-extending piezoelectric stack and an ultrasonic horn secured to and extending distally from the piezoelectric stack, the ultrasonic horn and the piezoelectric stack aligned on and sharing a longitudinal axis, the ultrasonic horn including:
      a body defining a tubular configuration having a hollow interior, the body defining a plurality of slots therethrough and into the hollow interior, the slots distally-spaced from the piezoelectric stack and extending longitudinally in parallel orientation relative to the longitudinal axis; and
      a nose extending distally from the body; and
   an elongated assembly extending distally from the handle assembly, the elongated assembly including a waveguide configured to engage the nose of the ultrasonic horn, the waveguide defining a blade at a distal end thereof,
   wherein ultrasonic energy produced by the piezoelectric stack is transmitted along the horn and the waveguide to the blade for treating tissue adjacent the blade.

2. The ultrasonic surgical instrument according to claim 1, wherein the body and the nose are monolithically formed as a single component from a zirconium-based amorphous metal.

3. The ultrasonic surgical instrument according to claim 1, wherein the ultrasonic horn defines a total mass of less than about 80 g.

4. The ultrasonic surgical instrument according to claim 1, wherein a thickness of each wall of the ultrasonic horn is between about 0.6 mm and about 4 mm.

5. The ultrasonic surgical instrument according to claim 1, wherein the ultrasonic horn defines a total length of less than about 100 mm.

6. The ultrasonic surgical instrument according to claim 1, wherein the plurality of slots are elongated slots equally-spaced about the body between a proximal end portion of the body and a node point defined towards a distal end of the body.

7. The ultrasonic surgical instrument according to claim 1, wherein the nose tapers in a proximal-to-distal direction.

8. The ultrasonic surgical instrument according to claim 1, wherein the nose is of solid construction except for a distal connector and defines a diameter between about 0.6 mm and about 4 mm.

* * * * *